United States Patent [19]
Bader

[11] Patent Number: 6,146,344
[45] Date of Patent: Nov. 14, 2000

[54] LOWER LIMB ORTHOTIC BRACE

[76] Inventor: Wade Bader, 13325 Golf Crest Cir., Tampa, Fla. 33634

[21] Appl. No.: 09/357,350

[22] Filed: Jul. 14, 1999

[51] Int. Cl.$^7$ ........................................................ A61F 5/00
[52] U.S. Cl. .......................... 602/6; 602/5; 602/7; 602/8; 602/9; 602/12; 602/16
[58] Field of Search .................................. 602/5, 6, 7, 8, 602/9, 12, 16; 128/846

[56] References Cited

U.S. PATENT DOCUMENTS

| | | | |
|---|---|---|---|
| 3,040,740 | 6/1962 | Parker | 602/12 |
| 3,682,163 | 8/1972 | Plummer | 602/12 |
| 5,158,530 | 10/1992 | Conklin | 602/8 |
| 5,573,501 | 11/1996 | Ruscito et al. | 602/7 |
| 5,624,386 | 4/1997 | Tailor et al. | 602/16 |

*Primary Examiner*—Michael A. Brown
*Assistant Examiner*—Lalita Hamilton
*Attorney, Agent, or Firm*—A. W. Fisher, III

[57] ABSTRACT

A lower limb orthotic brace to control the movement of the lower limb of a patient comprising a contoured orthotic contact shell and an integral load-bearing frame, the contoured orthotic contact shell comprises at least one layer of fabric impregnated with a hardened structural resin forming an inner orthotic contact surface conforming to the outer surface of the lower limb of the patient and the integral load-bearing frame comprises at least one reinforcing member extending along the contoured orthotic contact shell including a plurality of bundled continuous composite fibers woven in a multidirectional tubular braid impregnated with a hardened structural resin with at least one side of the braid in contact with the contoured orthotic contact shell along the entire length of the braid such that the hardened resins impregnating the fabric of the contoured orthotic contact shell combine with the resins impregnating the braid thereby forming a continuous integral structural matrix encapsulating both the braid and the contoured orthotic contact shell.

25 Claims, 6 Drawing Sheets

LOWER LIMB ORTHOTIC BRACE

BACKGROUND OF THE INVENTION

1. Field of the Invention

A lower limb orthotic brace to control the movement of the lower limb of a patient comprising a contoured otrhotic contact shell and an integral load-bearing frame.

2. Description of the Prior Art

Numerous efforts have been made to design and manufacture a light weight, durable orthotic brace. New materials now provide an opportunity to create new, more useful braces.

U.S. Pat. No. 5,817,041 shows a lower limb orthotic comprising a foot orthotic, a pair of lateral supporting members, a detached or removable anterior support member, a posterior support member, and strips of composite materials to resist plantar flexion, dorsiflexion and various of movements of the foot and ankle. The lateral supporting members further having strips of composite materials having fibers orientation substantially parallel to the length wise axis of the lateral supporting members. The foot orthotic and posterior supporting member further have composite strips extending across the bottom portion of the foot orthotic and rear side of the posterior supporting member respectively.

U.S. Pat. No. 5,693,007 teaches a method and apparatus for forming a custom fit knee orthosis including forming a flat preassembled knee orthosis of rigid carbon fiber and plastic resin composite material connected in a flat, rigid state by joint mechanisms.

U.S. Pat. No. 5,624,386 relates to an orthopedic brace using the shaped composite bars as integral components, and a method of thermoshaping the composite bars for use as filled components in the orthopedic brace are provided. The composite bars contain multiple fiber layers oriented in at least two directions with respect to the bar length to provide high flexural and torsional strength. The novel method of thermoshaping yields improved results over prior thermoshaping methods by providing an uncomplicated shaping capability while maintaining the structural and mechanical properties of the composite bar.

U.S. Pat. No. 5,573,501 shows a laminated, plastic orthotic device custom fitted to a wearer's extremity, typically a leg, wherein the orthotic includes a indicia bearing layer viewable on the outer surface of the orthotic. In one preferred embodiment, the device is fabricated from multiple layers of woven, reinforced and non-reinforced fabrics, adhesives, curable plastic resins and an image bearing layer. In other preferred embodiments, the device is fabricated of thermosetting plastic materials and an image bearing layer. The image layer may be comprised of woven fabric or non-woven materials which include drawings, insignias, photographs, textures or combinations thereof.

U.S. Pat. No. 5,154,690 discloses a supporter for mounting on a limb in position to cover an affected body portion to constrain and limit movement thereof comprising a tubular stretchable elastic material forming a main body and reinforcing member comprising an interlining laminated to a surface member which acts to restrict the elongation of said interlining.

U.S. Pat. No. 4,813,090 shows a hybrid composite material constructed from woven reinforced fabrics of Kevlar 49 and biaxially reinforced fibers of graphite and E-Glass bonded together with a thermosetting adhesive, for the application of custom orthotics. The material interlocks different fibers at different locations of the orthotic in order to take advantage of the unique properties of each reinforcing fibers. The resulting material creates a hybrid composite that exhibits a balance of properties, in both the longitudinal and transverse directions, unavailable with any single reinforcing fibers. A method of orthotic manufacturing involves a hand lat-up and forming procedure. The constructed composite material is formed and pressed on a prescribed cast, then allowed to cure under pressure. The post-cured material is stripped from the cast, then cut and ground and finally finished to the required orthotic. The produced orthotic combines the desired feature of a thin section with excellent combination of properties relevant to custom orthotics. Such properties include light weight, high strength and modulus, excellent resistance to impact, fatigue, and creep, and outstanding ability to damp vibrations.

U.S. Pat. No. 4,672,955 teaches the thigh and calf bands of a knee orthosis formed of a layer (or layers or curable composite material. The sidebars are integral with the thigh and calf bands in that they are simply extensions of the layers forming the thigh and calf bands. The sidebars are cured prior to fitting the thigh and calf bands about the leg, but the thigh and calf bands are left incured so that they may be formable about the leg and cured in place thereon.

SUMMARY OF THE INVENTION

The present invention relates to a lower limb orthotic brace for controlling the movement of the knee, ankle and foot of a patient by selectively isolating portions of the lower limb from forces transmitted between the lower limb and the ground through modulation of the distribution and magnitude of flexure in the lower limb orthotic brace.

The lower limb orthotic brace comprises a contoured orthotic contact shell with an integral load-bearing frame to receive the lower limb of the patient. The contoured orthotic contact shell is constructed of at least one layer of fabric impregnated with structural resin forming an inner orthotic contact surface conforming to the outer surface of the lower limb of the patient including an upper calf support section, an intermediate support section and a lower foot support section. The upper calf support section includes a flexible retaining strap to retain the device on the lower limb of the patient. At least one opening is formed in each of the upper, intermediate and lower support sections of the contoured orthotic contact shell to facilitate donning by the patient as well as to reduce the bulk and weight of the lower limb orthotic brace.

The load-bearing frame comprises at least one reinforcing member extending through the upper calf support section, the intermediate support section and the lower foot support section of lower limb orthotic brace. Each reinforcing member comprises a plurality of bundled continuous composite fibers combined in a multidirectional weave forming an initially flexible braided tube compressed into a substantially flat strip conforming to the shape of the contoured orthotic contact shell. Individual composite fibers may be formed from carbon, graphite, kevlar or other commercially available braided composite materials.

During the manufacturing process, the contoured orthotic contact shell and load-bearing frame are formed by applying the fabric of the contoured orthtic contact shell and the reinforcing members to a positive cast of the patient's lower limb. In forming the positive cast the patient's ankle and foot are placed in a selected theraputic orientation to facilitate improved function of the lower limb while the patient is standing or walking. The braided tube is compressed into a substantially flat strip against the outer surface of the contoured orthotic contact shell. The fabric and braided tube are then impregnated with structural resins under a vacuum. One side of the braid is maintained in continuous contact with the contoured orthotic contact shell along the entire length of the braid.

Structural resins impregnating the braid combine with the resin impregnating the fabric forming a continuous bond between the braid and the fabric throughout the length of the reinforcing member. An additional layer of fabric may be applied over the load-bearing frame to increase the bond between the integral load-bearing frame and the contoured orthotic contact shell or to conceal or cover the reinforcing members. Pigments may be added to the structural resins prior to introduction to the process in order to mimic skin tone or to create other decorative effects.

After the structural resins impregnating the fabric and braided tube have hardened, the positive cast is removed through openings formed in the contoured orthotic contact shell by cutting away portions of the fabric or shell to form the openings in the contoured orthotic contact shell without invading the braid or severing any of the bundled continuous composite fibers therein.

The selected degree of isolation of the ankle joint or foot of the patient is obtained through the flexure of the contoured orthotic contact shell, the magnitude and distribution of flexure in the contoured orthotic contact shell being modulated through the selective size, orientation, position, and number of openings in the contoured orthotic contact shell together with the selective size, orientation, position, and number of reinforcing members in the integral load-bearing frame. In applications where maximum isolation of the lower limb is desired, multiple reinforcing members may be disposed throughout the calf support section, the intermediate support section and the foot support section of the contoured orthotic contact shell. Where multiple reinforcing members are required, two or more braided tubes may be positioned side by side, stacked one on top of another or disposed telecopingly one within another.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE INVENTION

Figure 1:
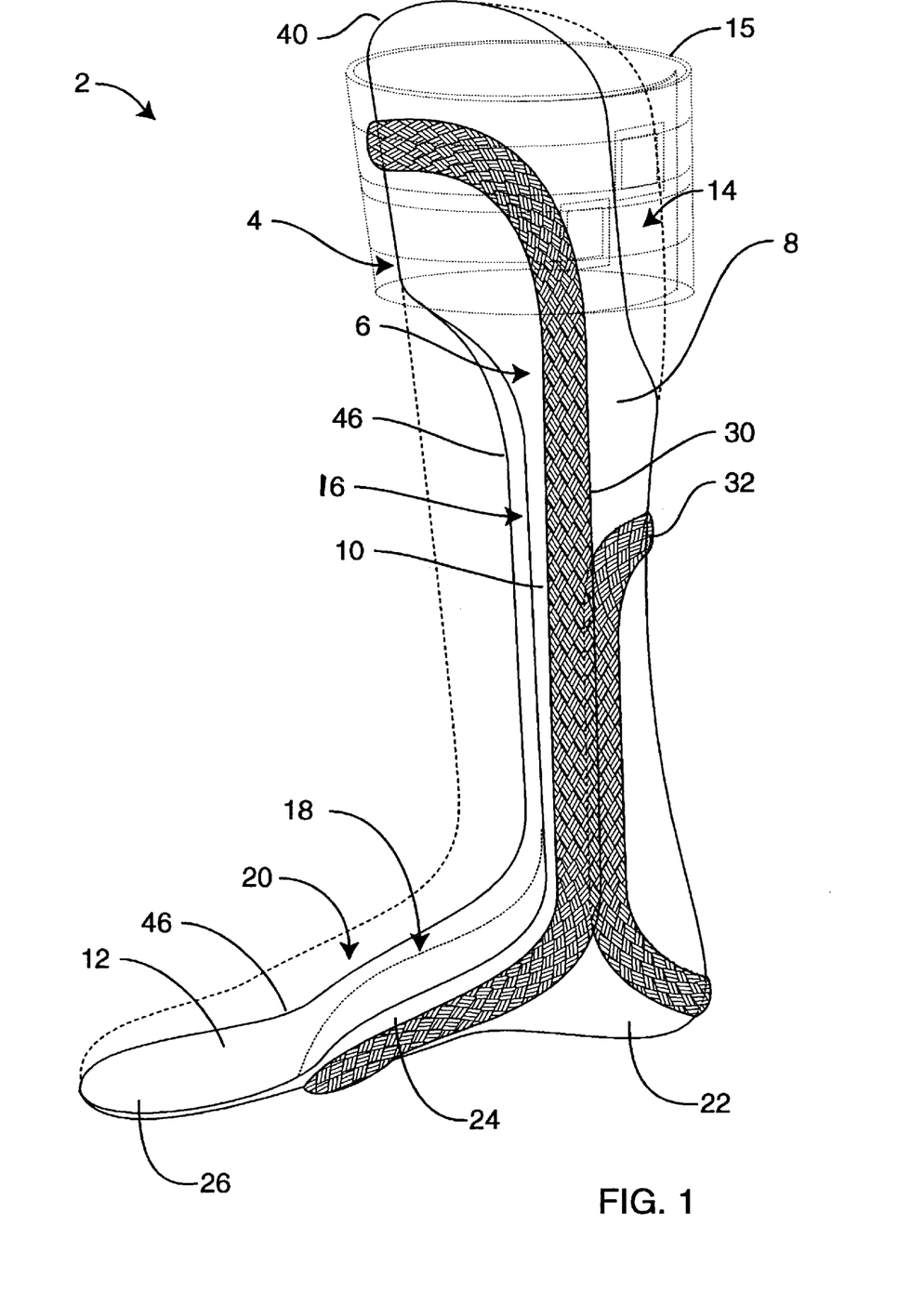
FIG. 1 is a side view of the lower limb orthotic brace of the present invention.

As shown in FIG. 1, the present invention relates to a lower limb orthotic brace generally indicated as 2 for controlling the movement of the knee, ankle and foot of a patient. The lower limb orthotic brace 2 comprises a contoured orthotic contact shell generally indicated as 4 having an integral load-bearing frame generally indicated as 6 integrally formed therewith and includes an upper calf support section 8, an intermediate support section 10 and a lower foot support section 12. At least one opening 14 is formed in the upper calf support section 8 to receive the lower limb of the patient (not shown) which is retained therein by a flexible calf strap 15 attached to the upper calf support section 8 and encircling the calf of the patient. At least one opening 16 is formed in the intermediate support section 10 to facilitate donning of lower limb orthotic brace 2 and to provide ventilation of the patient's lower limb. At least one additional opening 18 is formed in the lower foot support section of lower limb orthotic brace 2 to facilitate donning and to provide ventilation of the patient's foot. In other words, the opening 14 forms a posterior shell aperture or window and the openings 16 and 18 cooperatively form an anterior shell aperture or window. The lower foot support section 12 of the contoured orthotic contact shell 4 includes a solid foot support surface generally indicated as 20 having a heel section 22 to support the heel, a medial section 24 to support the arch of the foot and a forward section 26 to support the forefoot.

As further shown in FIG. 1, the integral load-bearing frame 6 includes a reinforcing member 30 extending through the upper calf support section 8, the intermediate support section 10 and the lower foot support section 12 of the contoured orthotic contact shell 4. As will be described in greater detail, one or more supplemental reinforcing members 32 may be positioned high-stress areas of the contoured orthotic contact shell 4 to reduce the amount of flexure therein.

Figure 3:
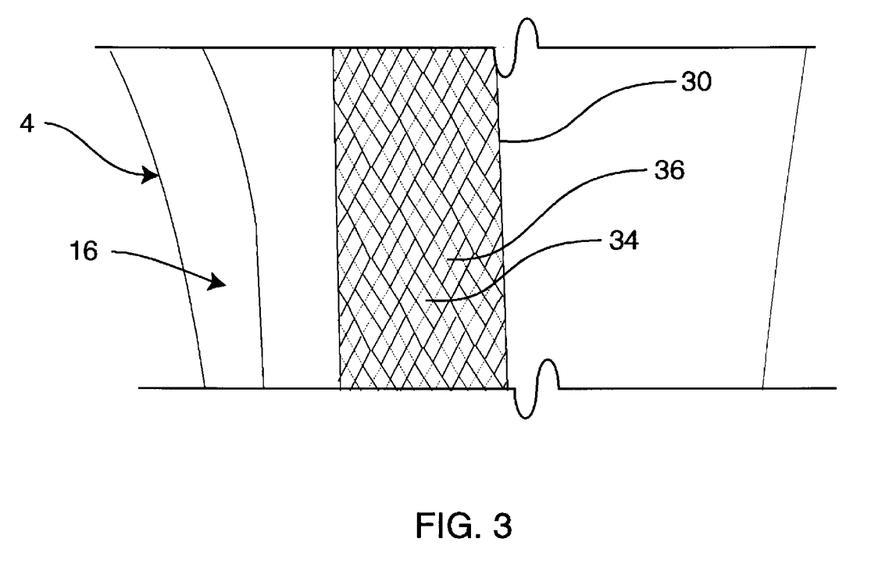
FIG. 3 is a detailed partial side vide of the contoured orthotic contact shell and reinforcing member of the present invention.

As best shown in FIG. 3, the reinforcing member 30 comprises a plurality of bundles each indicated as 34 of continuous composite fibers 36 woven together in a tubular multidirectional braid 38 impregnated with hardened structural resin. The multidirectional braid 38 may include one or more types of individual continuous composite fibers including graphite, carbon, kevlar or other commercially available materials.

Figure 2:
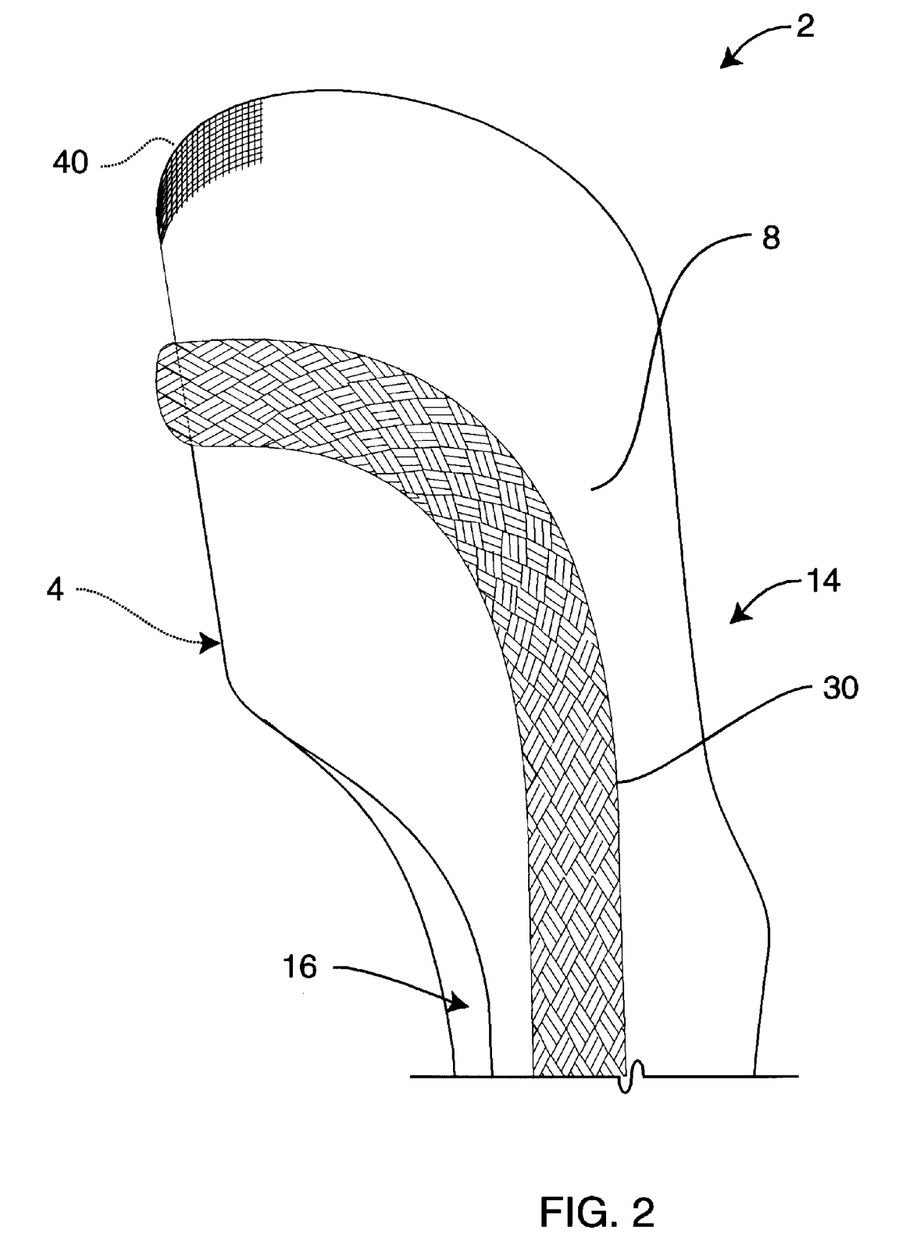
FIG. 2 is a detailed partial side view of the upper portion of the lower limb orthotic brace of the present invention.
Figure 4:
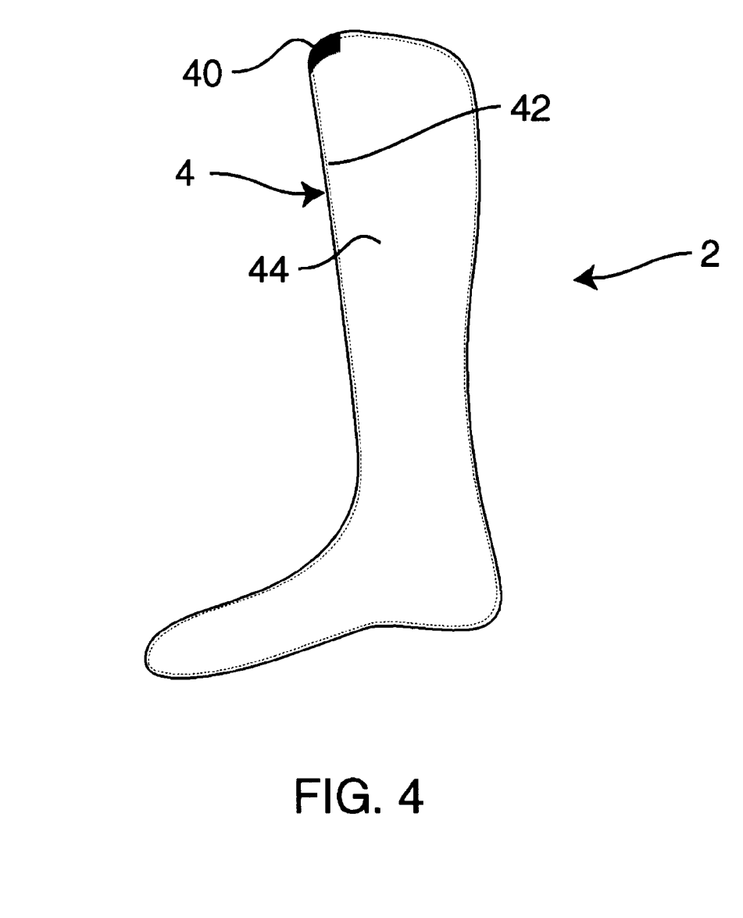
FIGS. 4 through 6 depict various stages of the method for producing the lower limb orthotic brace of the present invention.
Figure 5:
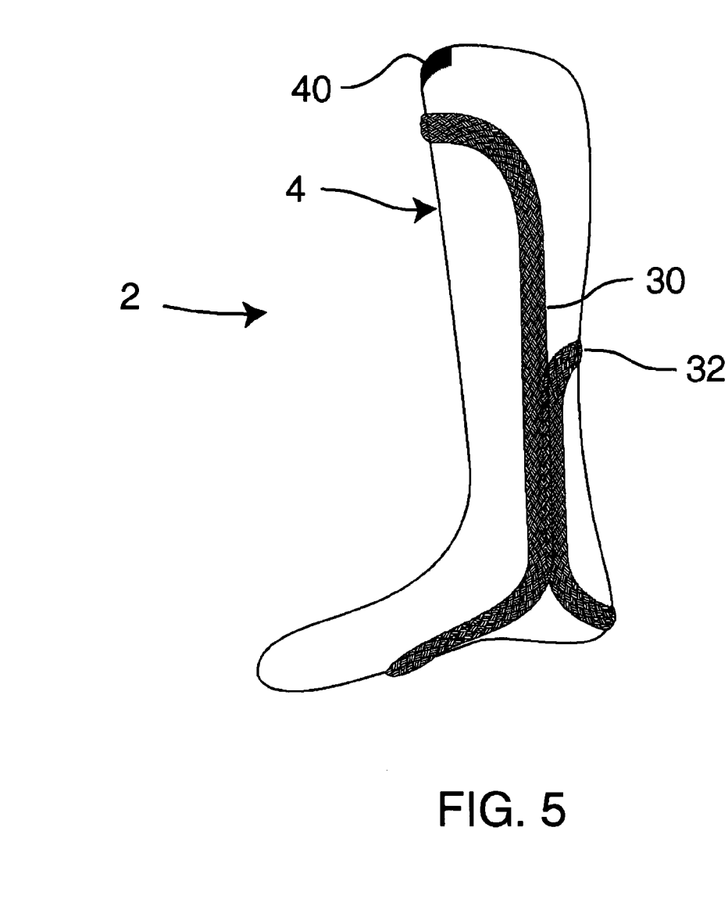
Figure 6:
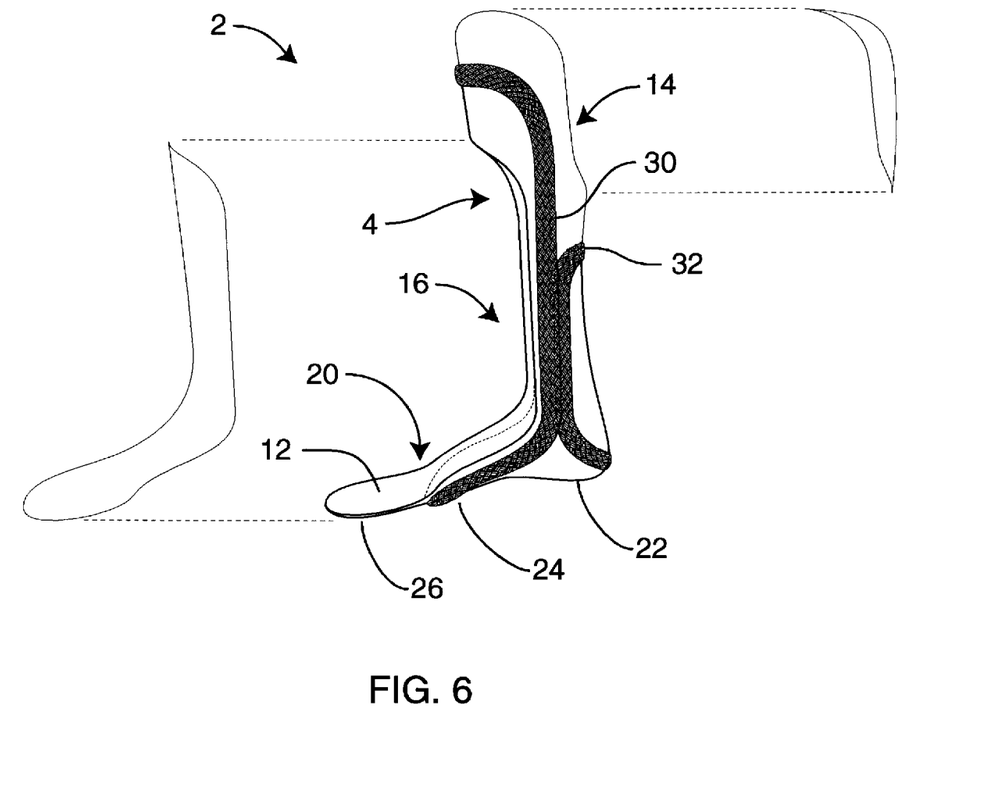

As shown in FIGS. 1 and 2, the contoured orthotic contact shell 2 comprises at least one layer of fabric 40 impregnated with hardened structural resin thereby forming a contoured inner contact surface conforming to the outer surface of the patient's lower limb. As shown in FIGS. 4 through 6, the contoured orthotic contact shell is constructed by applying fabric 40 to a positive cast 42 of the patient's lower limb with the patient's knee, ankle and foot being placed in a selected therapeutic position. The tubular multidirectional braid 38 is then compressed into a substantially flat strip against the outer surface 44 of the contoured orthotic contact shell 4 and placed within a plastic bag. A vacuum is then applied to the plastic bag and structural resins introduced to the top of the mold and drawn into the fabric 40 and the tubular multidirectional braid 38. As the structural resin impregnates the fabric 40 and the tubular multidirectional braid 38, the inner side of the tubular multidirectional braid 38 is maintained in continuous contact with the outer surface of the contoured orthotic contact shell 4 along the entire length of the tubular multidirectional braid 38. Structural resins impregnating the tubular multidirectional braid 38 combine with the resin impregnating the fabric 40 forming a continuous bond between the flattened tubular multidirectional braid 38 and the fabric 40 throughout the length of the reinforcing member 30.

An additional layer of fabric 40 may be applied over the contoured orthotic contact shell 4 and the integral load-bearing frame 8 to increase the bond between the integral load-bearing frame 8 and the contoured orthotic contact shell 4 or the reinforcing member 30. Pigments may also be added to the structural resins prior to introduction to the process in order to mimic skin tone or to create other decorative effects. After the structural resins impregnating the fabric 40 and braided tube 38 have hardened, the positive cast 42 is removed through the openings 14, 16 and 18 formed in the contoured orthotic contact shell 4 by cutting away portions of the fabric 40 without invading the braid or severing any of the bundled continuous composite fibers 38 therein.

In use, the selected degree of isolation of the ankle joint or foot of the patient is obtained through the flexure of the contoured orthotic contact shell 4, the magnitude and distribution of flexure in the contoured orthotic contact shell 4 being modulated through the selective size, orientation, position, and number of openings 14, 16, and 18 in the contoured orthotic contact shell 4 together with the selective size, orientation, position, and number of reinforcing members 30 and 32 in the integral load-bearing frame 8. In applications where maximum isolation of the lower limb is desired, multiple reinforcing members 30 may be disposed throughout the upper calf support section 10, the intermediate support section 12 and the lower foot support section 14 of the contoured orthotic contact shell 4. Where multiple reinforcing members 30 are required, two or more tubular multidirectional braids 38 may be positioned side by side, stacked one on top of another, or disposed telescopingly one within another.

As a result of the inherent strength of the continuous composite fibers 36, the lower limb orthtotic brace 2 of the present invention can be adapted to a variety of orthotic forms. As shown in FIG. 1, the present invention comprises a foot ankle orthosis or AFO. In order to achieve maximum isolation of the lower limb of the patient, substantially parallel reinforcing members 30 extend along each side of the patient's lower leg in the upper calf support section 8 through the intermediate support section 10 into the lower foot support section 12 of the contoured orthotic contact shell 4 in spaced relationship to the openings 16 and 18, and adjacent the peripheral edge 46 thereof. Supplemental reinforcing members 32 may be positioned adjacent to the substantially parallel reinforcing member 30 and extend downwardly into the lower foot support section 14 to reinforce the heel section 24 of the contoured orthotic contact shell 4.

Figure 7:
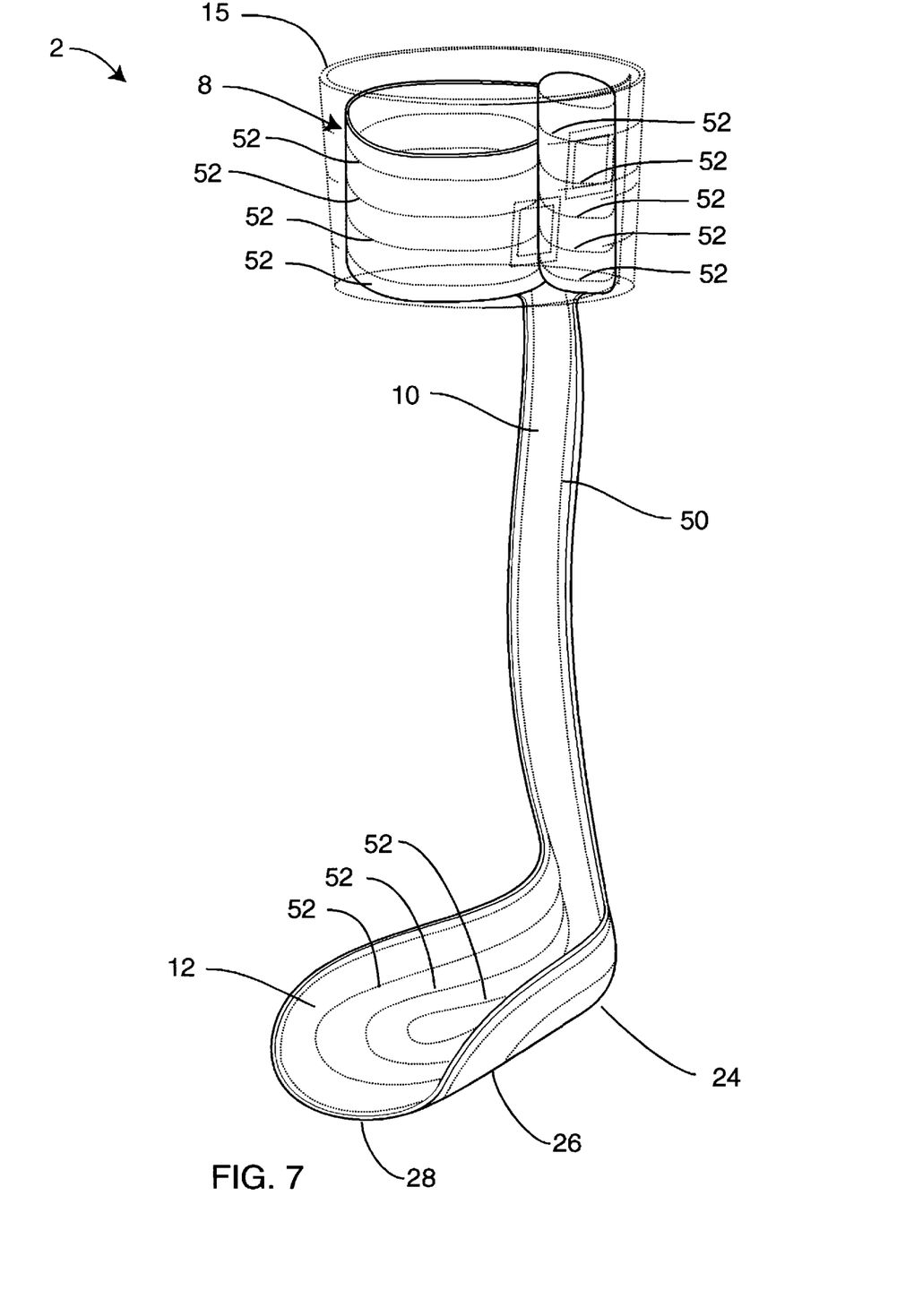
FIG. 7 is an alternate embodiment of the lower limb orthotic brace of the present invention.

As shown in FIG. 7, an alternative embodiment of the lower limb orthotc brace 2 comprises a floor reaction device comprising a reduced number or reinforcing elements. In this embodiment, a single posterior reinforcing element 50 extends between the upper calf support section 8 and the lower foot support section 12 through the intermediate support section 10, while multiple reinforcing members 52 are provided in the upper calf support section 8 and the lower foot support section 12. To provide for minimal movement of the foot, additional reinforcing members 52 may be positioned throughout the heel section 22, medial section 24 and forward section 26 of the lower foot support section 12 of the contoured orthotic contact shell 4. Where movement of the forefoot and or arch of the patient is desirable, reinforcing members may be limited to the heel section and rearward portions of the medial section, thereby allowing flexure in the medial and forward sections of the lower foot support section during ambulation.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A lower limb orthotic brace to control the movement of the lower limb of a patient comprising a contoured orthotic contact shell and an integral load-bearing frame, said contoured orthotic contact shell comprises at least one layer of fabric impregnated with a hardened structural resin forming an inner orthotic contact surface conforming to the outer surface of the lower limb of the patient and the integral load-bearing frame comprises at least one reinforcing member extending along said contoured orthotic contact shell including a plurality of bundled continuous composite fibers woven in a multidirectional tubular braid impregnated with a hardened structural resin with at least one side of said braid in contact with said contoured orthotic contact shell along the entire length of the braid such that the hardened resins impregnating said fabric of said contoured orthotic contact shell combine with the resins impregnating said braid thereby forming a continuous integral structural matrix encapsulating both said braid and said contoured orthotic contact shell.

2. The lower limb orthotic brace of claim 1 wherein said contoured orthotic contact shell comprises an upper calf support section and a lower foot support section.

3. The lower limb orthotic brace of claim 2 having an opening is formed in said upper support section and said lower support section of said contoured orthotic contact shell to facilitate donning by the patient.

4. The lower limb orthotic brace of claim 2 wherein said contoured orthotic contact shell and load-bearing frame are formed by applying said fabric of said contoured orthotic contact shell and said reinforcing member to a positive mold of a lower limb.

5. The lower limb orthotic brace of claim 4 wherein said braided tube is compressed into a substantially flat strip against the outer surface of said contoured orthotic contact shell and said fabric and said braided tube are impregnated with structural resins under a vacuum.

6. The lower limb orthotic brace of claim 5 wherein one side of said braid is maintained in continuous contact with said contoured orthotic contact shell along the entire length of said braid.

7. The lower limb orthotic brace of claim 5 wherein the positive cast is removed through openings formed in said contoured orthotic contact shell by cutting away portions of said fabric and said shell to form said openings in said contoured orthotic contact shell without invading said braid or severing any of the bundled continuous composite fibers therein after the structural resins impregnating the fabric and braided tube have hardened.

8. The lower limb orthotic brace of claim 7 wherein structural resins impregnating said tubular multidirectional braid combine with the resin impregnating said fabric forming a continuous bond between said flattened tubular multidirectional braid and the fabric through the length of said reinforcing member.

9. The lower limb orthotic brace of claim 1 wherein said reinforcing member extends through said upper calf support section and said lower foot support section of said contoured orthotic contact shell.

10. The lower limb orthotic brace of claim 1 further including supplemental reinforcing members positioned in high-stress areas of said contoured orthotic contact shell to reduce the amount of flexure therein.

11. The lower limb orthotic brace of claim 1 wherein said reinforcing member extends along each side of the patient's lower leg in said upper calf support section through an intermediate support section into said lower foot support section of said contoured orthotic contact shell.

12. A lower limb orthotic brace comprising a contoured orthotic contact shell including an upper calf support section, an intermediate support section, and a lower foot support section, the contoured orthotic contact shell having at least one opening positioned in a non load-bearing area thereof and an integral load-bearing frame comprising at least one reinforcing member comprising multiple composite fibers impregnated with a hardened structural resin with at least one side of the reinforcing member being in contact with the contoured orthotic contact shell along the entire length of the reinforcing member thereby forming a continuous structural matrix encompassing both the integral load-bearing frame and the contoured orthotic contact shell where the reinforcing members of the integral load bearing frame are positioned and aligned such that forces are transmitted between the ground and the lower limb of the wearer through the contoured orthotic contact shell and load bearing frame thereby isolating or immobilizing selected portions of the lower limb where the degree of isolation or immobilization is a function of the flexure of the contoured orthotic contact shell in reaction to the forces transmitted therein, the magnitude and distribution of flexure being modulated by the selective orientation, position and number of reinforcing members within the load-bearing frame in combination with the selective orientation, position and number of openings in the contoured orthotic contact shell.

13. The lower limb orthotic brace of claim 12 where the contoured orthotic contact shell comprises at least one layer of fabric impregnated with hardened structural resin.

14. The lower limb orthotic brace of claim of claim 12 where the composite fibers comprise a plurality of bundled composite fibers woven together in a multidirectional braid.

15. The lower limb orthotic brace of claim 14 where the substantially all of the individual composite fibers comprising the multidirectional braid extend through the substantially the entire length of the braid.

16. The lower limb orthotic brace of claim 15 where the multidirectional braid comprises a flattened tubular cross-section.

17. The lower limb orthotic brace of claim 16 where the structural resin impregnating the fabric in the contoured orthotic contact shell combine with the structural resin impregnating the braid thereby forming a continuous structural matrix encompassing both the braid and the fabric of the contoured orthotic contact shell and bonding the contoured orthotic contact shell and load-bearing frame into a integral unit.

18. The lower limb orthotic brace of claim 17 where the integral frame includes at least one reinforcing member extending from the upper calf support section through the intermediate support member to the lower foot support section.

19. The lower limb orthotic brace of claim 18 where multiple reinforcing members are positioned on opposite sides of the lower limb of the patient and extend from the intermediate support section to the lower foot support section of the contoured orthotic contact to substantially eliminate flexure of the contoured orthotic contact shell adjacent to the ankle joint of the patient.

20. The lower limb orthotic brace of claim 19 where one or more reinforcing members are positioned in the lower foot support section of the orthotic contact shell to substantially eliminate flexure of the orthotic contact shell adjacent to the mid foot of the patient.

21. The lower limb orthotic brace of claim 20 where an opening is provided in top wall and side walls of the frontal portion of the lower foot support section of the contoured orthotic contact shell in order to allow flexure of the contoured orthotic contact shell adjacent to the forefoot of the patient.

22. The lower limb orthotic brace of claim 18 with an opening in the intermediate support section adjacent to the front and both sides of the lower limb of the patient and having at least one or more reinforcing members extending from the upper calf support section through the intermediate section adjacent to the posterior surface of the lower limb of the patient to the lower foot support section of the contoured orthotic contact shell.

23. The lower limb orthotic brace of claim 22 where multiple reinforcing members are positioned in the intermediate section of the contoured orthotic contact shell to substantially eliminate flexure of the contoured orthotic contact shell adjacent to the ankle joint of the patient.

24. The lower limb orthotic brace of claim 23 where multiple reinforcing members combined in concentric alignment one within another.

25. The lower limb orthotic brace of claim 24 where the reinforcing member is selectively sized such as to allow flexure in the intermediate section of the contoured orthotic contact shell adjacent to the ankle joint of the patient.

* * * * *